United States Patent
Hissoiny

(10) Patent No.: US 10,493,299 B2
(45) Date of Patent: Dec. 3, 2019

(54) DETERMINING PARAMETERS FOR A BEAM MODEL OF A RADIATION MACHINE USING DEEP CONVOLUTIONAL NEURAL NETWORKS

(71) Applicant: Elekta, Inc., Atlanta, GA (US)

(72) Inventor: Sami Hissoiny, Longueuil (CA)

(73) Assignee: Elekta, Inc., Atlanta, GA (US)

( * ) Notice: Subject to any disclaimer, the term of this patent is extended or adjusted under 35 U.S.C. 154(b) by 173 days.

(21) Appl. No.: 15/836,539

(22) Filed: Dec. 8, 2017

(65) Prior Publication Data
US 2019/0175952 A1 Jun. 13, 2019

(51) Int. Cl.
*A61N 5/10* (2006.01)
*G06N 3/02* (2006.01)
(Continued)

(52) U.S. Cl.
CPC ........... *A61N 5/1077* (2013.01); *A61N 5/103* (2013.01); *A61N 5/1049* (2013.01); *G06N 3/02* (2013.01); *G06N 20/00* (2019.01); *G16H 20/40* (2018.01); *A61N 5/1031* (2013.01); *A61N 5/1036* (2013.01); *A61N 5/1039* (2013.01);
(Continued)

(58) Field of Classification Search
CPC .... A61N 5/1077; A61N 5/103; A61N 5/1049; A61N 5/1031; A61N 5/1036; A61N 5/1039; A61N 2005/1041; G06N 3/02; G06N 20/00; G06T 2207/10096;
(Continued)

(56) References Cited

U.S. PATENT DOCUMENTS 9,370,672 B2 * 6/2016 Parsai .................. A61N 5/1042
10,099,067 B2 * 10/2018 Kapatoes ............. A61N 5/1075
(Continued)

FOREIGN PATENT DOCUMENTS

EP       1917999       5/2008
WO       2014187866    11/2014
(Continued)

OTHER PUBLICATIONS

"International Application Serial No. PCT US2018 064102, International Search Report dated Apr. 9, 2019", 7 pgs.
(Continued)

*Primary Examiner* — Kiho Kim
(74) *Attorney, Agent, or Firm* — Schwegman Lundberg & Woessner, P.A.; Sanjay Agrawal

(57) ABSTRACT

Systems and methods can include training a deep convolutional neural network model to provide a beam model for a radiation machine, such as to deliver a radiation treatment dose to a subject. A method can include determining a range of parameter values for at least one parameter of a beam model corresponding to the radiation machine, generating a plurality of sets of beam model parameter values, wherein one or more individual sets of beam model parameter values can include a parameter value selected from the determined range of parameter values, providing a plurality of corresponding dose profiles respectively corresponding to respective individual sets beam model parameter values in the plurality of sets of beam model parameter values, and training the neural network model using the plurality of beam models and the corresponding dose profiles.

20 Claims, 9 Drawing Sheets

(51) Int. Cl.
*G16H 20/40* (2018.01)
*G06N 20/00* (2019.01)

(52) U.S. Cl.
CPC .............. *A61N 2005/1041* (2013.01); *G06T 2207/10096* (2013.01); *G06T 2207/10121* (2013.01); *G06T 2207/20084* (2013.01)

(58) Field of Classification Search
CPC ........... G06T 2207/10121; G06T 2207/20084; G16H 20/40
See application file for complete search history.

(56) References Cited

U.S. PATENT DOCUMENTS

| | | | |
|---|---|---|---|
| 2014/0235923 A1* | 8/2014 | McNutt | A61N 5/1031 600/1 |
| 2014/0263990 A1* | 9/2014 | Kawrykow | A61N 5/1031 250/252.1 |
| 2016/0166855 A1* | 6/2016 | Kumar | A61N 5/1039 600/1 |
| 2017/0151445 A1* | 6/2017 | Luan | A61N 5/10 |
| 2017/0259082 A1* | 9/2017 | Bzdusek | A61N 5/103 |
| 2018/0090299 A1* | 3/2018 | Nakayamada | H01J 37/3026 |
| 2019/0192880 A1* | 6/2019 | Hibbard | A61N 5/1039 |

FOREIGN PATENT DOCUMENTS

| | | |
|---|---|---|
| WO | 2014205128 | 12/2014 |
| WO | 2016081916 | 5/2016 |

OTHER PUBLICATIONS

"International Application Serial No. PCT US2018 064102, Written Opinion dated Apr. 9, 2019", 8 pgs.
"International Application Serial No. PCT US2018 064102, Invitation to Pay Additional Fees dated Feb. 18, 2019", 13 pgs.
Wolfgang, A Tome, "Beam Modeling for a Convolution Superposition-Based Treatment Planning System", (Mar. 10, 2001).

* cited by examiner

DETERMINING PARAMETERS FOR A BEAM MODEL OF A RADIATION MACHINE USING DEEP CONVOLUTIONAL NEURAL NETWORKS

TECHNICAL FIELD

Embodiments of the present invention pertain generally to determining parameters for a beam model of a radiation machine. In particular, the present invention pertains to using deep learning technologies to determine beam model parameters of a radiation machine.

OVERVIEW

Radiotherapy is used to treat cancers and other ailments in mammalian (e.g., human and animal) tissue. An exemplary radiotherapy is provided using a linear accelerator (LINAC), whereby a target (e.g., a tumor) is irradiated by high-energy particles (e.g., electrons, photons, ions and the like). In a typical LINAC-based radiation treatment, multiple radiation beams are directed towards the target from different angles.

The surrounding normal tissue is often called an organ at risk (OAR). To prevent OARs from the severe collateral damage caused by the radiation beams, the doses received by these OARs should be limited to a certain level. Such limitations on the doses received by the OARs, often called constraints, need to be satisfied during treatment planning.

Treatment planning is a process involving determination of specific radiotherapy parameters (e.g., radiation beam angles, radiation intensity level at each angle, etc.) for implementing a treatment goal under the constraints.

The outcome of the treatment planning exercise is a radiotherapy treatment plan, hereinafter also referred to as a treatment plan or simply a plan. A typical treatment planning process includes delineating one or more targets and one or more OARs from a medical image of the patient, specifying radiation beam angles, or a range of angles in the case of an arc plan, and determining an aperture shape or shapes and radiation intensity levels for each shape at each beam angle.

The treatment planning includes a beam model that can include parameters that describe, among other things, the energy distribution of radiation emitted from the radiation machine (e.g., a LINAC). The beam model parameter values can vary between radiation machines, even radiation machines that are the same model—in each radiation machine there can be small differences, such as in fluence or energy provided by the radiation machine. Mechanical differences (e.g., mechanical dimensions or material properties) or differences in component values (e.g., electronic circuit component values) between the radiation machines can lead to the differences in beam model parameter values between different radiation machines. In certain approaches, after the radiation machine is installed, and final tuning is performed, a customer can perform measurements using a phantom that simulates patient tissue. The phantom can include a tank of water with a moveable dosimeter inside the tank of water. A beam modeler can then perform beam modeling using the measurements to determine the beam model parameter values for the radiation machine corresponding to the measurements. However, the beam modeling as performed by the beam modeler can be time consuming. The beam modeling can include an iterative process that includes many dose calculations (e.g., approximately 50-100 dose calculations) that can take approximately ten minutes each.

The inventors have recognized, among other things, that the beam modeling process can be greatly improved by using machine learning (e.g., a neural network model), such as to reduce the time taken for beam modeling. However, using data sets corresponding to existing radiation machines may be undesirable, such as due to errors introduced during the measurement of dose profiles. The inventors have recognized, among other things, that synthesized data sets can provide training data free from measurement errors, such as those that can be introduced during the measurement of dose profiles (e.g., a percent depth dose profile or radial dose profile). Additionally, the inventors have recognized that a number of data sets corresponding to existing radiation machines may be inadequate for machine learning to produced beam model parameters with a desired accuracy. The inventors have recognized that additionally, data sets can be synthesized and used to compensate for a shortage of data sets, such as that caused by a limited number of radiation machines with known beam model parameter values. By reducing the time taken for beam modeling, such as by using machine learning, radiation machines can be commissioned at a faster rate which can lead to improved patient workflows and improved patient outcomes.

The above overview is intended to provide an overview of subject matter of the present patent application. It is not intended to provide an exclusive or exhaustive explanation of the invention. The detailed description is included to provide further information about the present patent application.

In an aspect, the disclosure can feature a computer implemented method for training a deep convolutional neural network model, such as to provide a beam model for a radiation machine to deliver a radiation treatment dose to a subject. The method can include determining a range of parameter values for at least one parameter of a beam model corresponding to the radiation machine. The method can also include generating a plurality of sets of beam model parameter values, wherein one or more individual sets of beam model parameter values can include a parameter value selected from the determined range of parameter values. The method can also include providing a plurality of corresponding dose profiles respectively corresponding to respective individual sets beam model parameter values in the plurality of sets of beam model parameter values. The method can also include training the neural network model using the plurality of beam models and the corresponding dose profiles. The method can also include training the neural network model using at least one set of beam model parameter values and corresponding measured dose profiles previously collected from at least one radiation machine. Determining the range of beam model parameter values for at least one beam model parameter can include determining a beam model parameter value for each of a plurality of radiation machines. The method can also include measuring at least one dose profile for each of a plurality of radiation machines. Training the neural network model can include providing N sets of generated beam model parameter values and corresponding dose profiles to the neural network model. Training the neural network model can also include providing dose profiles from M radiation machines and corresponding beam model parameters to the neural network model. The method can also include randomly or pseudo-randomly selecting the beam model parameter value, from the determined range of beam model parameter values, such as for generating at least one of the sets of beam model parameter values. Respective sets of beam model parameter values can be generated using a plurality of dose profiles, wherein an individual dose profile of the plurality of corresponding dose profiles can include a relative dose of radiation that can vary with depth into a target sample. Determining a range of beam model parameter values for at least one parameter of a beam model can include determining a plurality of beam model parameter values related to an energy distribution of photons emitted from a radiation source of the radiation machine. The beam model parameters can include at least one of a size of a radiation source, a position of a radiation source, or an energy spectrum of a radiation source. Determining a range of beam model parameter values for at least one parameter of a beam model can include determining a plurality of beam model parameter values related to an energy distribution of electrons emitted from a radiation source of the radiation machine.

In an aspect, the disclosure can feature a computer implemented method of using a deep convolutional neural network, such as to determine at least one parameter value of a beam model for a radiation machine. The method can include receiving a trained neural network model previously trained using a plurality of sets of beam model parameter values and corresponding dose profiles, the trained neural network model being trained for predicting at least one radiation machine beam model parameter value from one or more measured radiation machine dose profiles. The method can also include measuring a plurality of dose profiles from the radiation machine, such as to be provided as an input to the trained neural network model. The method can also include determining at least one beam model parameter value of a set of beam model parameter values for the radiation machine using the trained neural network model. The method can also include calculating a dose profile from a set of beam model parameter values that can include the determined at least one beam model parameter value and comparing the calculated dose profile to a measured dose profile. The set of beam model parameter values can include at least one beam model parameter value that is not determined using the trained neural network model. The method can also include updating the at least one beam model parameter value determined by the neural network model if a difference between the measured dose profile from the radiation machine and the determined dose profile meets a specified criterion. The method can also include determining a plurality of dose profiles using a set of beam model parameter values that can include the at least one beam model parameter value determined by the neural network model, where individual ones of the plurality of dose profiles can correspond to a different field size of the radiation machine. The method can also include comparing each of the plurality of determined dose profiles to a corresponding one of a plurality of measured dose profiles. Receiving a neural network previously trained using a plurality of sets of beam model parameter values and corresponding dose profiles can include receiving a trained neural network previously trained according to a method that includes determining a range of beam model parameter values for at least one parameter of a beam model corresponding to the radiation machine, generating a plurality of sets of beam model parameter values, wherein one or more individual sets of beam model parameter values can include a parameter value selected from the determined range of parameter values, providing a plurality of corresponding dose profiles respectively corresponding to respective individual sets of beam model parameter values in the plurality of sets of beam model parameter values, and training the neural network using the plurality of sets of beam model parameter values and the corresponding dose profiles. The method can also include using the set of beam model parameter values with the determined at least one beam model parameter value to estimate a dose of radiation from the radiation machine to target region within a patient.

In an aspect, the disclosure can feature a system for generating at least beam model parameter value of a beam model for a radiation machine from at least one measured dose profile of the radiation machine. The system can include an interface that can be configured to receive at least one measured dose profile corresponding to the radiation machine and receive a neural network model for estimating at least one beam model parameter value of the radiation machine. The system can also include a memory for storing the neural network model and the at least one measured dose profile, wherein the neural network model can be trained using a plurality of sets of beam model parameter values and corresponding dose profiles. The system can also include a processor configured to estimate at least one beam model parameter value of the radiation machine using the at least one measured dose profile as an input to the neural network model. The stored neural network model can be trained by determining a range of beam model parameter values for at least one parameter of a beam model corresponding to the radiation machine, generating a plurality of sets of beam model parameter values, wherein one or more individual sets of beam model parameter values can include a parameter value selected from the determined range of parameter values, providing a plurality of corresponding dose profiles respectively corresponding to respective individual sets of beam model parameter values in the plurality of sets of beam model parameter values, and providing the plurality of sets of beam model parameter values and the corresponding dose profiles to the neural network model. The interface can be configured to transmit a set of beam model parameter values including the beam model parameter value estimated by the neural network model and corresponding dose profiles to a user if a difference between the measured dose profile from the radiation machine and a dose profile determined from the set of beam model parameter values meets a specified criterion.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
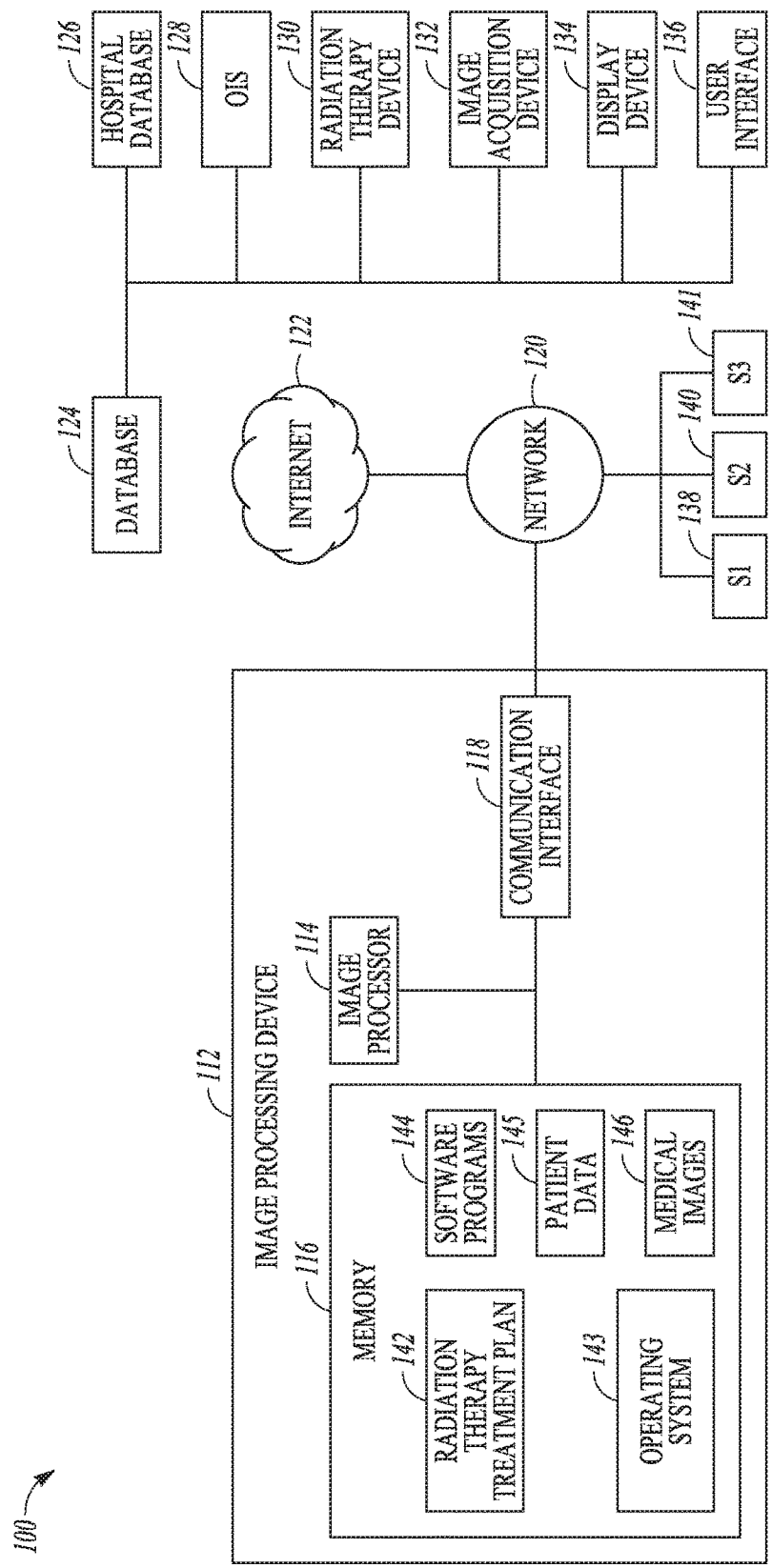
FIG. 1 illustrates an exemplary radiotherapy system, according to some embodiments of the present disclosure.

In the following detailed description, reference is made to the accompanying drawings which form a part hereof, and which is shown by way of illustration-specific embodiments in which the present invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not be taken in a limiting sense, and the scope of the present invention is defined by the appended claims and their equivalents.

Radiation machines used for radiotherapy can provide a radiation beam (e.g., a photon beam, or an electron beam) to a patient, such as to irradiate a tumor in the patient. Prior to treatment, treatment planning can be performed, such as by a clinician. During the treatment planning, the clinician can decide how to best irradiate the tumor while minimizing damage to neighboring OARs. A beam model for the radiation machine can be used during the treatment planning process to simulate the radiation exiting the radiation machine and impinging upon the patient. Determining values for beam model parameters can be an iterative, and time consuming process. Each dose calculation can take approximately 10 minutes and many dose calculations can take many hours to complete. The relatively long time to complete dose calculations can cause delays in using the radiation machine for patient treatment. The inventors have recognized among other things, that the beam modeling process can be greatly improved by using machine learning (e.g., a neural network model). However, using data sets corresponding to existing radiation machines may be undesirable, such as due to errors introduced during the measurement of dose profiles. The inventors have recognized, among other things, that synthesized data sets can provide training data free from measurement errors, such as those that can be introduced during the measurement of dose profiles (e.g., a percent depth dose profile or radial dose profile). The inventors have also recognized that a neural network model typically requires a large number of data sets (e.g., at least one thousand data sets) to provide accurate training of the model, and that such a large number of data sets may not be available, such as due to a limited number of radiation machines with known beam model parameter values. The inventors have recognized that new data sets can be synthesized and used to compensate for a shortage of data sets, such as that caused by a limited number of radiation machines with known beam model parameter values. The synthesized data sets can then be used to train the neural network model. By reducing the time taken for beam modeling, radiation machines can be commissioned at a faster rate which can lead to improved patient workflows and improved patient outcomes.

FIG. 1 illustrates an exemplary radiotherapy system 100 for providing radiation therapy to a patient. The radiotherapy system 100 includes an image processing device, 112. The image processing device 112 may be connected to a network 120. The network 120 may be connected to the Internet 122. The network 120 can connect the image processing device 112 with one or more of a database 124, a hospital database 126, an oncology information system (ON) 128, a radiation therapy device 130, an image acquisition device 132, a display device 134, and a user interface 136. The image processing device 112 can be configured to generate radiation therapy treatment plans 142 to be used by the radiation therapy device 130.

The image processing device 112 may include a memory device 116, a processor 114 and a communication interface 118. The memory device 116 may store computer executable instructions, such as an operating system 143, a radiation therapy treatment plans 142 (e.g., original treatment plans, adapted treatment plans and the like), software programs 144 (e.g., artificial intelligence, deep learning, neural networks, radiotherapy treatment plan software), and any other computer-executable instructions to be executed by the processor 114. In one embodiment, the software programs 144 may convert medical images of one format (e.g., MRI) to another format (e.g., CT) by producing synthetic images, such as a pseudo-CT image. For instance, the software programs 144 may include image processing programs to train a predictive model for converting a medial image 146 in on modality (e.g., an MRI image) into a synthetic image of a different modality (e.g., a pseudo CT image); alternatively, the trained predictive model may convert a CT image into an MRI image. In another embodiment, the software programs 144 may register the patient image (e.g., a CT image or an MR image) with that patient's dose distribution (also represented as an image) so that corresponding image voxels and dose voxels are associated appropriately by the network. In yet another embodiment, the software programs 144 may substitute functions of the patient images such as signed distance functions or processed versions of the images that emphasize some aspect of the image information. Such functions might emphasize edges or differences in voxel textures, or any other structural aspect useful to neural network learning. In another embodiment, the software programs 144 may substitute functions of the dose distribution that emphasize some aspect of the dose information. Such functions might emphasize steep gradients around the target, or any other structural aspect useful to neural network learning. The memory device 116 may store data, including medical images 146, patient data 145, and other data required to create and implement a radiation therapy treatment plan 142.

In addition to the memory 116 storing the software programs 144, it is contemplated that software programs 144 may be stored on a removable computer medium, such as a hard drive, a computer disk, a CD-ROM, a DVD, a HD, a Blu-Ray DVD, USB flash drive, a SD card, a memory stick, or any other suitable medium; and the software programs 144 when downloaded to image processing device 112 may be executed by image processor 114.

The processor 114 may be communicatively coupled to the memory device 116, and the processor 114 may be configured to execute computer executable instructions stored thereon. The processor 114 may send or receive medical images 146 to memory 116. For example, the processor 114 may receive medical images 146 from the image acquisition device 132 via the communication interface 118 and network 120 to be stored in memory 116. The processor 114 may also send medical images 146 stored in memory 116 via the communication interface 118 to the network 120 be either stored in database 124 or the hospital database 126.

Further, the processor 114 may utilize software programs 144 (e.g., a treatment planning software) along with the medical images 146 and patient data 145 to create the radiation therapy treatment plan 142. Medical images 146 may include information such as imaging data associated with a patient anatomical region, organ, or volume of interest segmentation data. Patient data 145 may include information such as (1) functional organ modeling data (e.g., serial versus parallel organs, appropriate dose response models, etc.); (2) radiation dosage data (e.g., dose-volume histogram (DVH) information or (3) other clinical information about the patient and course of treatment (e.g., other surgeries, chemotherapy, previous radiotherapy, etc.).

In addition, the processor 114 may utilize software programs to generate intermediate data such as updated parameters to be used, for example, by a neural network model; or generate intermediate 2D or 3D images, which may then subsequently be stored in memory 116. The processor 114 may subsequently then transmit the executable radiation therapy treatment plan 142 via the communication interface 118 to the network 120 to the radiation therapy device 130, where the radiation therapy plan will be used to treat a patient with radiation. In addition, the processor 114 may execute software programs 144 to implement functions such as image conversion, image segmentation, deep learning, neural networks, and artificial intelligence. For instance, the processor 114 may execute software programs 144 that train or contour a medical image; such software 144 when executed may train a boundary detector, or utilize a shape dictionary.

The processor 114 may be a processing device, include one or more general-purpose processing devices such as a microprocessor, a central processing unit (CPU), a graphics processing unit (GPU), an accelerated processing unit (APU), or the like. More particularly, the processor 114 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processor 114 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some embodiments, the processor 114 may be a special-purpose processor, rather than a general-purpose processor. The processor 114 may include one or more known processing devices, such as a microprocessor from the Pentium™, Core™, Xeon™, or Itanium™ family manufactured by Intel™, the Turion™, Athlon™, Sempron™, Opteron™, FX™, Phenom™ family manufactured by AMD™, or any of various processors manufactured by Sun Microsystems. The processor 114 may also include graphical processing units such as a GPU from the GeForce®, Quadro®, Tesla® family manufactured by Nvidia™, GMA, Iris™ family manufactured by Intel™, or the Radeon™ family manufactured by AMD™. The processor 114 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor, for example, a multi-core design or a plurality of processors each having a multi-core design. The processor 114 can execute sequences of computer program instructions, stored in memory 116, to perform various operations, processes, methods that will be explained in greater detail below.

The memory device 116 can store medical images 146. In some embodiments, the medical images 146 may include one or more MRI image (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), Computed Tomography (CT) images (e.g., 2D CT, Cone beam CT, 3D CT, 4D CT), ultrasound images (e.g., 2D ultrasound, 3D ultrasound, 4D ultrasound), Positron Emission Tomography (PET) images, X-ray images, fluoroscopic images, radiotherapy portal images. Single-Photo Emission Computed Tomography (SPECT) images, computer generated synthetic images (e.g., pseudo-CT images) and the like. Further, the medical images 146 may also include medical image data, for instance, training images, and ground truth images, contoured images, and dose images. In an embodiment, the medical images 146 may be received from the image acquisition device 132. Accordingly, image acquisition device 132 may include a MRI imaging device, a CT imaging device, a PET imaging device, an ultrasound imaging device, a fluoroscopic device, a SPECT imaging device, an integrated Linear Accelerator and MRI imaging device, or other medical imaging devices for obtaining the medical images of the patient. The medical images 146 may be received and stored in any type of data or any type of format that the image processing device 112 may use to perform operations consistent with the disclosed embodiments. The memo device 116 may be a non-transitory computer-readable medium, such as a read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including image, data, or computer executable instructions (e.g., stored in any format) capable of being accessed by the processor 114, or any other type of computer device. The computer program instructions can be accessed by the processor 114, read from the ROM, or any other suitable memory location, and loaded into the RAM for execution by the processor 114. For example, the memory 116 may store one or more software applications. Software applications stored in the memory 116 may include, for example, an operating system 143 for common computer systems as well as for software-controlled devices. Further, the memory 116 may store an entire software application, or only a part of a software application, that are executable by the processor 114. For example, the memory device 116 may store one or more radiation therapy treatment plans 142.

The image processing device 112 can communicate with the network 120 via the communication interface 118, which can be communicatively coupled to the processor 114 and the memory 116. The Communication interface 118 may provide communication connections between the image processing device 112 and radiotherapy system 100 components (e.g., permitting the exchange of data with external devices). For instance, the communication interface 118 may in some embodiments have appropriate interfacing circuitry to connect to the user interface 136, which may be a hardware keyboard, a keypad, or a touch screen through which a user may input information into radiotherapy system 100.

Communication interface 118 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a WiFi adaptor), a telecommunication adaptor (e.g., 3G, 4G/LTE and the like), and the like. Communication interface 118 may include one or more digital and/or analog communication devices that permit image processing device 112 to communicate with other machines and devices, such as remotely located components, via the network 120.

The network 120 may provide the functionality of a local area network (LAN), a wireless network, a cloud computing environment (e.g., software as a service, platform as a service, infrastructure as a service, etc.), a client-server, a wide area network (WAN), and the like. For example, network 120 may be a LAN or a WAN that may include other systems S1 (138), S2 (140), and S3 (141). Systems S1, S2, and S3 may be identical to image processing device 112 or may be different systems. In some embodiments, one or more of systems in network 120 may form a distributed computing/simulation environment that collaboratively performs the embodiments described herein. In some embodiments, one or more systems S1, S2, and S3 may include a CT scanner that obtain CT images (e.g., medical images 146). In addition, network 120 may be connected to internet 122 to communicate with servers and clients that reside remotely on the internet.

Therefore, network 120 can allow data transmission between the image processing device 112 and a number of various other systems and devices, such as the OIS 128, the radiation therapy device 130, and the image acquisition device 132. Further, data generated by the OIS 128 and/or the image acquisition device 132 may be stored in the memory 116, the database 124, and/or the hospital database 126. The data may be transmitted/received via network 120, through communication interface 118 in order to be accessed by the processor 114, as required.

The image processing device 112 may communicate with database 124 through network 120 to send/receive a plurality of various types of data stored on database 124. For example, database 124 may include machine data that is information associated with a radiation therapy device 130, image acquisition device 132, or other machines relevant to radiotherapy. Machine data information may include radiation beam size, arc placement, beam on and off time duration, machine parameters, segments, multi-leaf collimator (MLC) configuration, gantry speed, MRI pulse sequence, and the like. Database 124 may be a storage device and may be equipped with appropriate database administration software programs. One skilled in the art would appreciate that database 124 may include a plurality of devices located either in a central or a distributed manner.

In some embodiments, database 124 may include a processor-readable storage medium (not shown). While the processor-readable storage medium in an embodiment may be a single medium, the term "processor-readable storage medium" should be taken to include a single medium or multiple media (e.g., a centralized or distributed database, and/or associated caches and servers) that store the one or more sets of computer executable instructions or data. The term "processor-readable storage medium" shall also be taken to include any medium that is capable of storing or encoding a set of instructions for execution by a processor and that cause the processor to perform any one or more of the methodologies of the present disclosure. The term "processor readable storage medium" shall accordingly be taken to include, but not be limited to, solid-state memories, optical and magnetic media. For example, the processor readable storage medium can be one or more volatile, non-transitory, or non-volatile tangible computer-readable media.

Image processor 114 may communicate with database 124 to read images into memory 116 or store images from memory 116 to database 124. For example, the database 124 may be configured to store a plurality of images (e.g., 3D MRI, 4D MRI, 2D MRI slice images, CT images, 2D Fluoroscopy images, X-ray images, raw data from MR scans or CT scans. Digital Imaging and Communications in Medicine (DIMCOM) data, etc.) that the database 124 received from image acquisition device 132. Database 124 may store data to be used by the image processor 114 when executing software program 144, or when creating radiation therapy treatment plans 142. Database 124 may store the data produced by the trained neural network including the network parameters constituting the model learned by the network and the resulting predicted data. The image processing device 112 may receive the imaging data 146 (e.g., 2D MRI slice images, CT images, 2D Fluoroscopy images, X-ray images, 3D MRI images, 4D MRI images, etc.) either from the database 124, the radiation therapy device 130 (e.g., a MRI-Linac), and or the image acquisition device 132 to generate a treatment plan 142.

In an embodiment, the radiotherapy system 100 can include an image acquisition device 132 that can acquire medical images (e.g., Magnetic Resonance Imaging (MRI) images, 3D MR, 2D streaming MRI, 4D volumetric MRI, Computed Tomography (CT) images, Cone-Beam CT, Positron Emission Tomography (PET) images, functional MRI images (e.g., fMRI, DCE-MRI and diffusion MRI), X-ray images, fluoroscopic image, ultrasound images, radiotherapy portal images, single-photo emission computed tomography (SPECT) images, and the like) of the patient. Image acquisition device 132 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the imaging acquisition device 132 can be stored within database 124 as either imaging data and/or test data By way of example, the images acquired by the imaging acquisition device 132 can be also stored by the image processing device 112, as medical image data 146 in memory 116.

In an embodiment, for example, the image acquisition device 132 may be integrated with the radiation therapy device 130 as a single apparatus (e.g., a MRI device combined with a linear accelerator, also referred to as an "MRI-Linac." Such an MRI-Linac can be used, for example, to determine a location of a target organ or a target tumor in the patient, so as to direct radiation therapy accurately according to the radiation therapy treatment plan 142 to a predetermined target.

The image acquisition device 132 can be configured to acquire one or more images of the patient's anatomy for a region of interest (e.g., a target organ, a target tumor or both). Each image, typically a 2D image or slice, can include one or more parameters (e.g., a 2D slice thickness, an orientation, and a location, etc.). In an embodiment, the image acquisition device 132 can acquire a 2D slice in any orientation. For example, an orientation of the 2D slice can include a sagittal orientation, a coronal orientation, or an axial orientation. The processor 114 can adjust one or more parameters, such as the thickness and/or orientation of the 2D slice, to include the target organ and/or target tumor. In an embodiment, 2D slices can be determined from information such as a 3D MRI volume. Such 2D slices can be acquired by the image acquisition device 132 in "near real-time" while a patient is undergoing radiation therapy treatment, for example, when using the radiation therapy device 130. "Near real-time" meaning acquiring the data in at least milliseconds or less.

The image processing device 112 may generate and store radiation therapy treatment plans 142 for one or more patients. The radiation therapy treatment plans 142 may provide information about a particular radiation dose to be applied to each patient. The radiation therapy treatment plans 142 may also include other radiotherapy information, such as beam angles, dose-histogram-volume information, the number of radiation beams to be used during therapy, the dose per beam, and the like.

The image processor 114 may generate the radiation therapy treatment plan 142 by using software programs 144 such as treatment planning software, such as Monaco®, manufactured by Elekta AB of Stockholm, Sweden. In order to generate the radiation therapy treatment plans 142, the image processor 114 may communicate with the image acquisition device 132 (e.g., a CT device, a MRI device, a PET device, an X-ray device, an ultrasound device, etc.) to access images of the patient and to delineate a target, such as a tumor. In some embodiments, the delineation of one or more organs at risk (OARs), such as healthy tissue surrounding the tumor or in close proximity to the tumor may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, the radiotherapy system 100 may study the dose distribution not only in the target, but also in the OAR.

In order to delineate a target organ or a target tumor from the OAR, medical images, such as MRI images, CT images, PET images, fMRI images, X-ray images, ultrasound images, radiotherapy portal images, SPECT images and the like, of the patient undergoing radiotherapy may be obtained non-invasively by the image acquisition device 132 to reveal the internal structure of a body part. Based on the information from the medical images, a 3D structure of the relevant anatomical portion may be obtained. In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker using a program such as MONACOT™ manufactured by Elekta AB of Stockholm, Sweden) or automatically (e.g., using a program such as the Atlas-based auto-segmentation software, ABAS™, manufactured by Elekta AB of Stockholm, Sweden). In certain embodiments, the 3D structure of a target tumor or an OAR may be generated automatically by the treatment planning software.

After the target tumor and the OAR(s) have been located and delineated, a dosimetrist, physician or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and beam-on times. During the inverse-planning process, the physician may define dose constraint parameters that set bounds on how much radiation an OAR may receive (e.g., defining full dose to the tumor target and zero dose to any OAR; defining 95% of dose to the target tumor; defining that the spinal cord, brain stem, and optic structures receive ≤45 Gy, ≤55 Gy and <54 Gy, respectively). The result of inverse planning may constitute a radiation therapy treatment plan 142 that may be stored in memory 116 or database 124. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the image processing device 112 can generate a tailored radiation therapy treatment plan 142 having these parameters in order for the radiation therapy device 130 to provide radiotherapy treatment to the patient.

In addition, the radiotherapy system 100 may include a display device 134 and a user interface 136. The display device 134 may include one or more display screens that display medical images, interface information, treatment planning parameters (e.g., contours, dosages, beam angles, etc.) treatment plans, a target, localizing a target and/or tracking a target, or any related information to the user. The user interface 136 may be a keyboard, a keypad, a touch screen or any type of device that a user may input information to radiotherapy system 100. Alternatively, the display device 134 and the user interface 136 may be integrated into a device such as a tablet computer, e.g., Apple iPad®, Lenovo Thinkpad®, Samsung Galaxy®, etc.

Furthermore, any and all components of the radiotherapy system 100 may be implemented as a virtual machine (e.g., VMWare, Hyper-V, and the like). For instance, a virtual machine can be software that functions as hardware. Therefore, a virtual machine can include at least one or more virtual processors, one or more virtual memories, and one or more virtual communication interfaces that together function as hardware. For example, the image processing device 112, the OIS 128, the image acquisition device 132 could be implemented as a virtual machine. Given the processing power, memory, and computational capability available, the entire radiotherapy system 100 could be implemented as a virtual machine.

FIG. 2A illustrates an exemplary radiation therapy device 202 that may include a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 can include one or more attenuators or collimators, such as a multi-leaf collimator (MLC).

Referring back to FIG. 2, a patient can be positioned in a region 212, supported by the treatment couch 216 to receive a radiation therapy dose according to a radiation therapy treatment plan. The radiation therapy output 204 can be mounted or attached to a gantry 206 or other mechanical support. One or more chassis motors (not shown) may rotate the gantry 206 and the radiation therapy output 204 around couch 216 when the couch 216 is inserted into the treatment area. In an embodiment, gantry 206 may be continuously rotatable around couch 216 when the couch 216 is inserted into the treatment area. In another embodiment, gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable m transverse direction ("T"), moveable m a lateral direction ("L"), or as rotation about one or more other axes, such as rotation about a transverse axis (indicated as "R"). A controller communicatively connected to one or more actuators (not shown) may control the couch 216 movements or rotations in order to properly position the patient m or out of the radiation beam 208 according to a radiation therapy treatment plan. As both the couch 216 and the gantry 206 are independently moveable from one another in multiple degrees of freedom, which allows the patient to be positioned such that the radiation beam 208 precisely can target the tumor.

Figure 2:
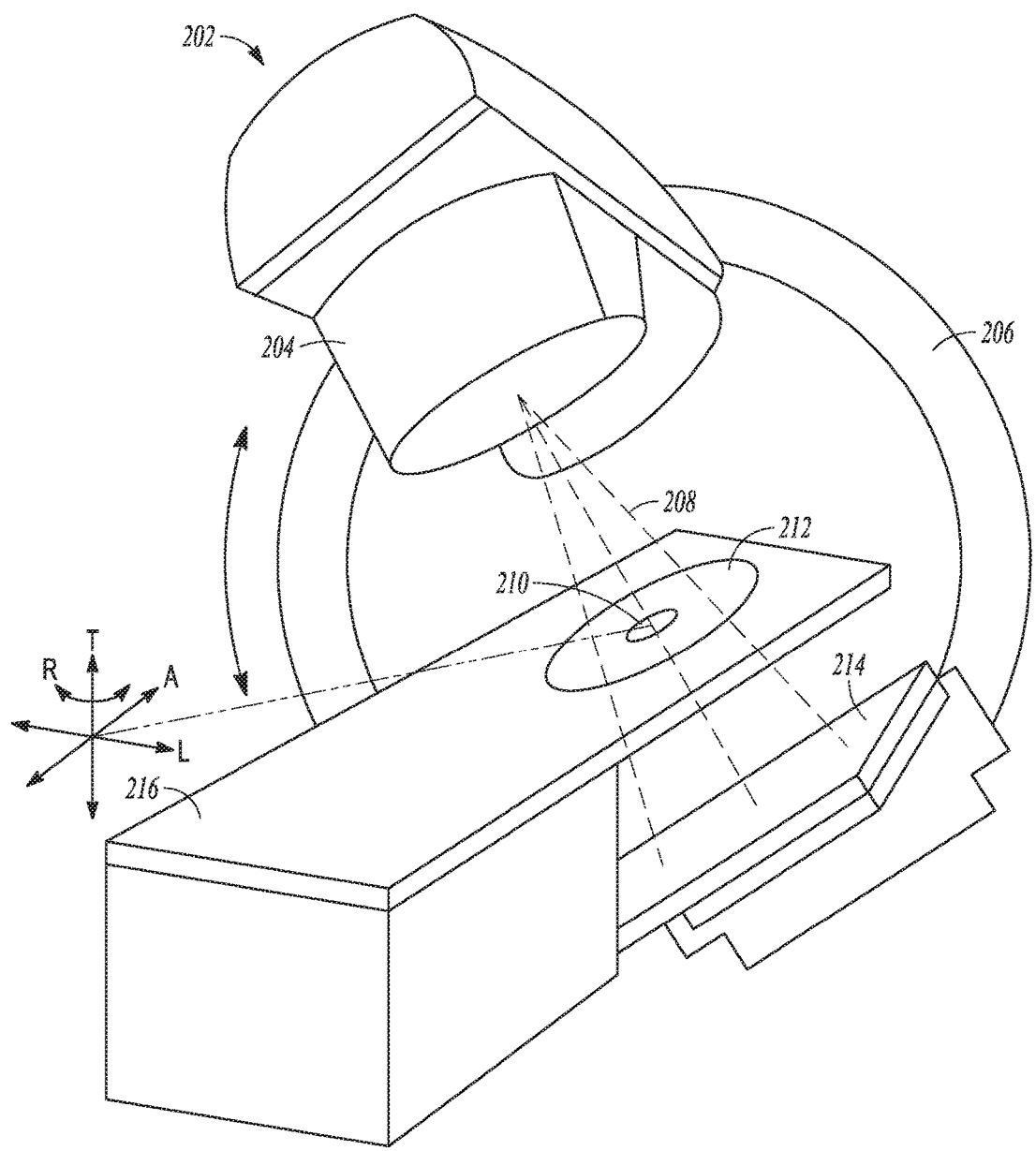
FIG. 2 illustrates an exemplary radiation therapy system that can include radiation therapy output configured to provide a therapy beam.

The coordinate system (including axes A, T, and L) shown in FIG. 2 can have an origin located at an isocenter 210. The isocenter can be defined as a location where the central axis of the radiation therapy beam 208 intersects the origin of a coordinate axis, such as to deliver a prescribed radiation dose to a location on or within a patient. Alternatively, the isocenter 210 can be defined as a location where the central axis of the radiation therapy beam 208 intersects the patient for various rotational positions of the radiation therapy output 204 as positioned by the gantry 206 around the axis A.

Gantry 206 may also have an attached imaging detector 214. The imaging detector 214 preferably located opposite to the radiation source 204, and in an embodiment, the imaging detector 214 can be located within a field of the therapy beam 208.

The imaging detector 214 can be mounted on the gantry 206 preferably opposite the radiation therapy output 204, such as to maintain alignment with the therapy beam 208. The imaging detector 214 rotating about the rotational axis as the gantry 206 rotates. In an embodiment, the imaging detector 214 can be a flat panel detector (e.g., a direct detector or a scintillator detector). In this manner, the imaging detector 214 can be used to monitor the therapy beam 208 or the imaging detector 214 can be used for imaging the patient's anatomy, such as portal imaging. The control circuitry of radiotherapy device 202 may be integrated within system 100 or remote from it.

In an illustrative embodiment, one or more of the couch 216, the therapy output 204, or the gantry 206 can be automatically positioned, and the therapy output 204 can establish the therapy beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially, but can intersect in a desired therapy locus on or within the patient, such as at the isocenter 210. A prescribed cumulative dose of radiation therapy can thereby be delivered to the therapy locus while damage to tissue nearby the therapy locus can be reduced or avoided.

FIG. 2 generally illustrates an embodiment of a radiation therapy device configured to provide radiotherapy treatment to a patient, including a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another embodiment, the therapy output can be fixed, such as located in a region laterally separated from the patient, and a platform supporting the patient can be used to align a radiation therapy isocenter with a specified target locus within the patient. In another embodiment, a radiation therapy device can be a combination of a linear accelerator and an image acquisition device. In some embodiments, the image acquisition device may be an MRI, an X-ray, a CT, a CBCT, a spiral CT, a PET, a SPECT, an optical tomography, a fluorescence imaging, ultrasound imaging, or radiotherapy portal imaging device, etc., as would be recognized by one of ordinary skill in the art.

Figure 3:
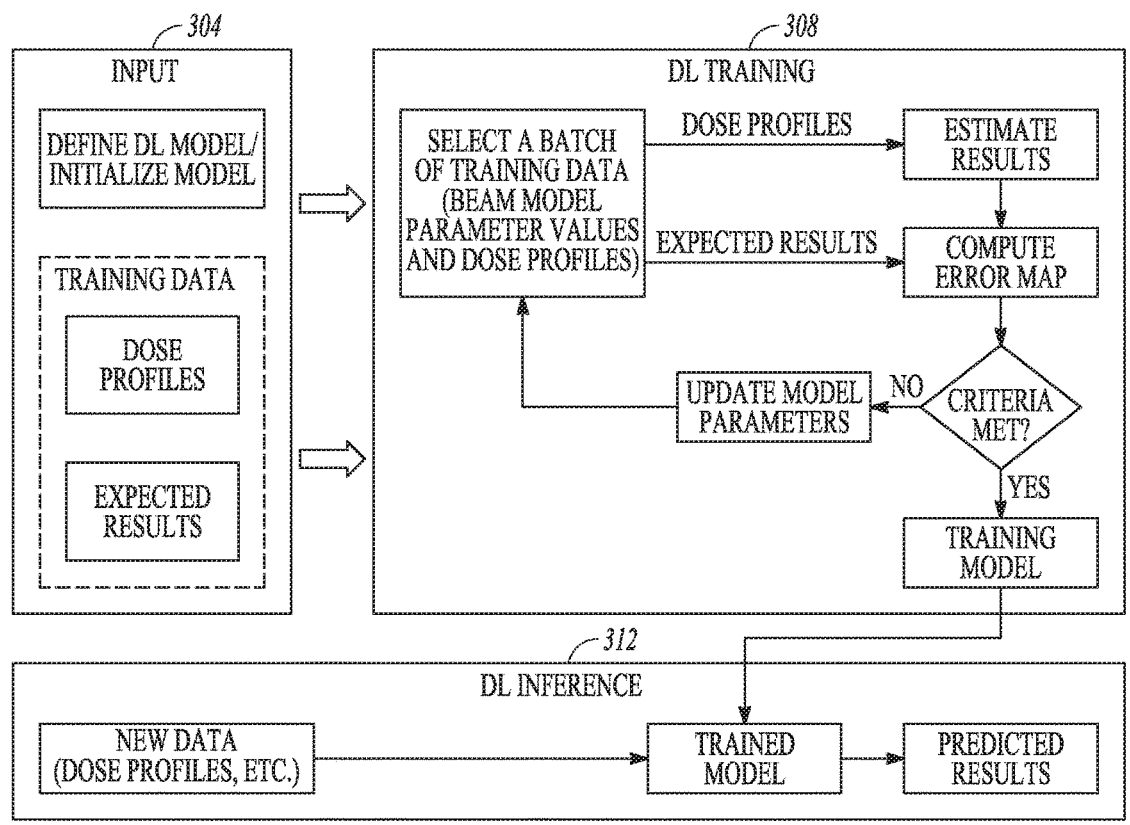
FIG. 3 illustrates an exemplary flow diagram for deep learning.

FIG. 3 illustrates an exemplary flow diagram for deep learning, where a deep learning model, such as a deep convolutional neural network can be trained and used to determine beam model parameter values for a radiation machine. Inputs 304 can include a defined deep learning model having an initial set of values and training data. The training data can include dose profiles and expected results. The deep learning model can include a neural network, such as a deep convolutional neural network. The deep leaning network can be trained on dose profiles, such as percent depth dose curves and the corresponding beam parameters. When trained, the deep learning network can produce an estimate of such beam model parameter values for a radiation machine using only percent depth dose curves for that radiation machine. The expected results can include percent depth dose curves that can be used in dose calculations during treatment planning. The beam model parameters can include a size and position of one or more photon sources within the radiation machine, a maximum energy of a photon spectrum for photons emitted from the radiation machine, a number of factors describing the shape of a photon spectrum emitted from the radiation machine. The beam model parameters can also include a size and position of one or more electron sources within the radiation machine, an average energy of an electron spectrum emitted from the radiation machine. The beam model parameters can also include one or more numbers describing how radiation (e.g., electrons or photons) emitted by the radiation machine can vary off-axis. During training of deep learning model 308, a batch of training data can be selected from the dose profiles and expected results (e.g., corresponding beam model parameter values). The selected training data can include at least one dose profile and the corresponding ground truth beam model parameter values. The deep leaning model can be applied to the selected dose profiles to provide estimated results (e.g., estimated beam model parameters), which can then be compared to the expected results (e.g., ground truth beam model parameter values corresponding to the selected dose profiles), to compute a difference that can provide an indication of training errors. The errors can be used during a procedure called backpropagation to correct the errors in parameters of the deep learning network (e.g., layer node weights and biases), such as to reduce or minimize errors in the beam model parameter value estimates during subsequent trials. The errors can be compared to predetermined criteria, such as proceeding to a sustained minimum for a specified number of training iterations. If the errors do not satisfy the predetermined criteria, then model parameters of the deep learning model can be updated using backpropagation, and another batch of training data can be selected from the dose profiles and expected results for another iteration of deep learning model training. If the errors satisfy the predetermined criteria, then the training can be ended and the trained model can then be used during a deep learning testing or inference stage 312 to predict beam model parameter values based on dose profiles different from the training data. The trained model can receive new dose profiles and provide predicted results (e.g., beam model parameter values).

Figure 4:
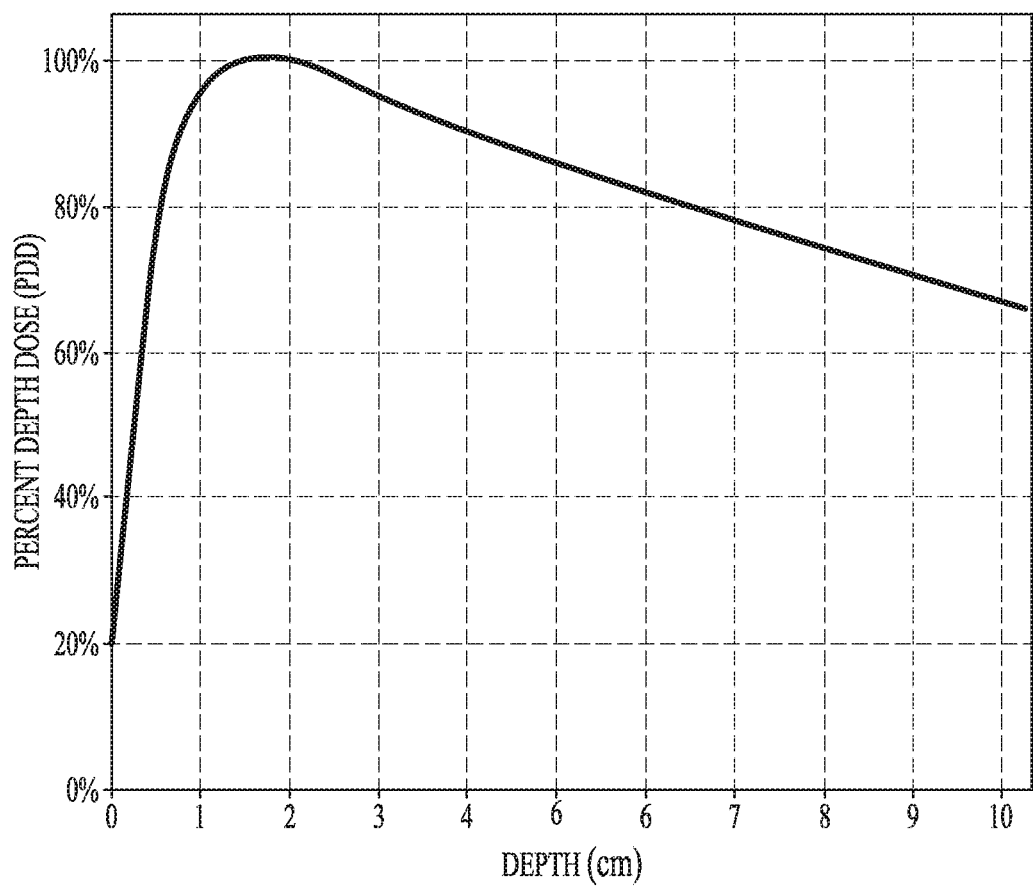
FIG. 4 illustrates an exemplary dose profile.

FIG. 4 illustrates an example of a percent depth dose curve. The percent depth dose curve can be measured by applying radiation from a radiation machine to a medium (e.g., a phantom) that simulates human tissue. In an example, the phantom can include water. The amount of radiation deposited as a function of depth in the medium can be measured and recorded, such as to provide a percent depth dose curve as illustrated in FIG. 4. Sensors installed in the medium can provide a measure of the deposited radiation.

Figure 5A:
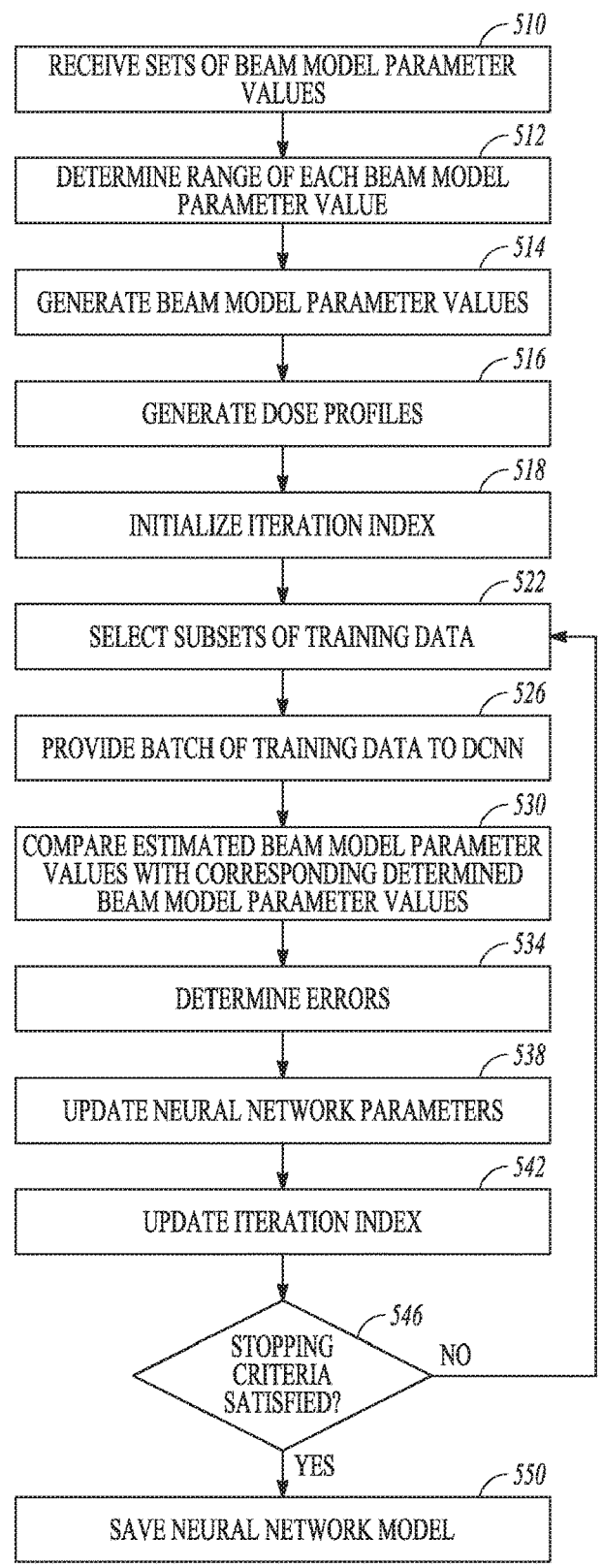
FIG. 5A illustrates an exemplary method for training a neural network model.

FIG. 5A illustrates an example of a method for training a neural network model, such as a deep convolutional neural network (DCNN) model for determining beam model parameter values of a radiation machine based on at least one measured dose profile from the radiation machine. Sets of beam model parameter values can be received, where each set of beam model parameter values can correspond to a radiation machine (step 510). A set of beam model parameter values can be represented by the expression $X=\{\varphi_1, \varphi_2, \varphi_3, \ldots \varphi_n\}$, where X can represent a set of beam model parameter values and $\varphi_j$, can represent a beam model parameter value of the $j^{th}$ beam model parameter. A range (e.g., minimum value and maximum value) for individual beam model parameter values can then be determined by analysis of beam parameter values from different sets of beam model parameter values (step 512). In an example where a value of a beam model parameter can be 0.1, 0.5, or 0.9 in a first, second, and third set of beam model parameters, respectively, a range of the beam model parameter value can be from 0.1 to 0.9. Sets of beam model parameter values can then be generated, such as by a random, or pseudo-random sampling of beam parameter values falling within the determined ranges (step 514). For example, N sets of beam model parameter values can be generated. In an example, the sampling can extend beyond the determined ranges by an amount (e.g., ±10%). Certain beam model parameter values may not vary significantly between different radiation machines. Such beam model parameter values can be the same for one or more sets of beam model parameter values. For example, the value of the beam model parameter $\varphi_3$ can be the same for one or more sets of beam model parameter values. The number N of sets of generated beam model parameter values can be selected to be large enough to facilitate training of the neural network model. For example, N can be greater than one thousand. Such a large number N, can be much greater than the number of radiation machines in existence (e.g., approximately 4000).

In an example, the number of sets of generated beam model parameters can be selected to cover the range of possible parameter values for all radiation machines, such as can lead to a reduced number of sets of generated beam parameters. Covering the range of possible parameter values for one beam model parameter can include generating a number of values within a range of possible parameter values. The number of values can be regularly, randomly, or pseudo-randomly spaced. A beam model radiation parameter can have a minimum value and a maximum value that can be determined, such as based on beam model parameter values determined by a beam modeler for a plurality of radiation machines. In an example, a minimum value of a beam model radiation parameter can be 1, a maximum value of the beam model radiation parameter can be 2, and a number of values covering the range of possible parameters can include 1.0, 1.2, 1.4, 1.6, 1.8, and 2.0. In an example where the number of sets of generated beam model parameters can be selected to cover the range of possible parameter values for all radiation machines, the number of sets can be less than the number of radiation machines in existence. Dose profiles can then be computed for each of the sets of generated beam parameters (step 516). The dose profiles can be determined by a computer implemented algorithm. In an embodiment where the dose profile can be determined by a computer algorithm, the algorithm can be an analytical algorithm and the computation can require several hours. Dose profiles for one or more field sizes can be determined for each of the sets of generated beam parameter values. The dose profiles can be computed both on-axis and off-axis. A dose depth profile can be computed along a central axis (e.g., along a direction of a radiation beam), and a radial dose profile can be computed at a specified depth along a direction orthogonal to the central axis (e.g., along a direction across the radiation beam). Additionally, the dose profiles can be computed for a range of field sizes (e.g., 1×1, 2×2, etc.). To begin network training, an iteration index can be set to an initial value of zero (step 518) A batch of training data can be formed from a number M of sets of beam model parameter values and corresponding dose profiles (step 522), where M can be less than N. The batch of training data can be provided to the neural network model and the neural network parameters can be updated based thereon (step 526). The neural network model can provide an output set of beam model parameter values based on one or more dose profiles in the batch of training data and current parameters of the neural network model (step 530). A comparison can be made between the output set of beam model parameter values corresponding to the received dose profiles in the batch of training data and ground truth beam model parameter values. Corresponding error sets, where each error value can include the difference between the estimated beam model parameter values and the corresponding ground truth beam model parameters are determined from the comparison (step 534). Parameters of the neural network model can then be updated based on the corresponding errors, such as by using backpropagation (step 538). In an embodiment, parameters of the neural network model can be updated, such as to minimize or reduce a function, such as the function $J(\Theta^*)=\arg\min_\Theta \|Y-Y^*\|^2$, where Y can represent the beam model parameter values determined by the neural network model, where $Y^*$ can represent the known beam model parameter values corresponding to the batch of training data, and where $\Theta^*$ can represent parameters of the neural network model (e.g., layer node weights and biases) corresponding to a minimized square error between Y and $Y^*$. After updating the parameters of the neural network model, the iteration index can be incremented by a value of one (step 542). The iteration index can correspond to a number of times that the parameters of the neural network model have been updated. Stopping criteria can be computed (step 546), and if the stopping criteria are satisfied, then the neural network model can be saved in a memory, such as the memory device 116 of image processing device 112 and the training can be halted (step 550). If the stopping criteria are not satisfied, then the training can continue at step 522. In an embodiment, additional training data can be generated as described above with respect to steps 514 and 516 before the training continues at step 522. In an embodiment, the stopping criteria can include a value of the iteration index (e.g., the stopping criteria can include whether the iteration index is greater than or equal to a determined maximum number of iterations). In an embodiment, the stopping criteria can include an accuracy of the output set of beam model parameter values (e.g. the stopping criteria can include whether the difference between the output set of beam model parameter values and the beam model parameter values corresponding to the received sets of medical images in the batch of training data is smaller than a threshold). In an embodiment, the threshold can correspond to an asymptotic minimum of all errors determined in step 534. In an embodiment, the beam model parameters can be presented to the neural network model in the form of images with fixed formats. In an embodiment, the dose profiles can be pooled with beam model parameter values and can be presented as real arrays.

Figure 5B:
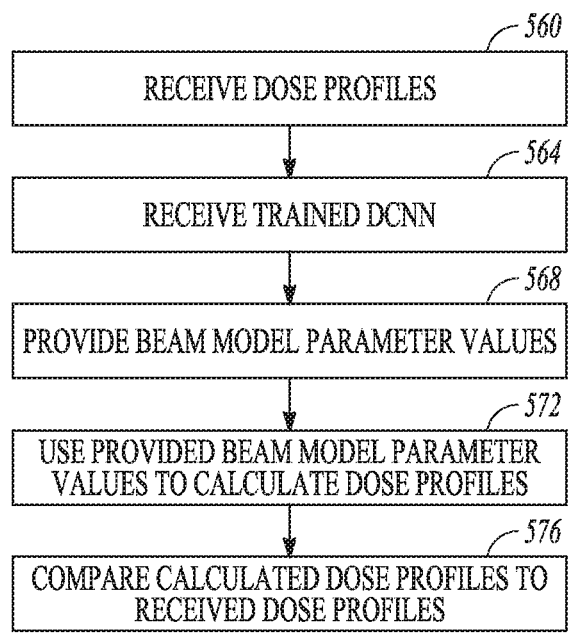
FIG. 5B illustrates an exemplary method for generating beam model parameters using a neural network model.

FIG. 5B illustrates an example of a method for generating beam model parameters using a trained neural network model, such as a deep convolutional neural network (DCNN) that can be trained according to the method described above with respect to FIG. 5A. Dose profiles can be received from a measurement device (step 560). A trained neural network model can be received from a network, such as the network 120, or from a memory, such as the memory device 116 of image processing device 112 (step 564). The trained neural network model can be used to determine beam model parameter values, such as for radiation treatment planning or replanning (step 568). The determined beam model parameter values can be used, such as automatically, or by a beam modeler, to calculate one or more dose profiles (step 572). The one or more calculated dose profiles can then be compared to one or more dose profiles, such as those received at step 560. If a difference between the one or more dose profiles received at step 56) and the one or more dose profiles calculated at step 572 meets a specified criterion, at least one beam model parameter value can be updated (step 576). For example, the at least one beam model parameter value can be updated by a beam modeler.

Figure 6:
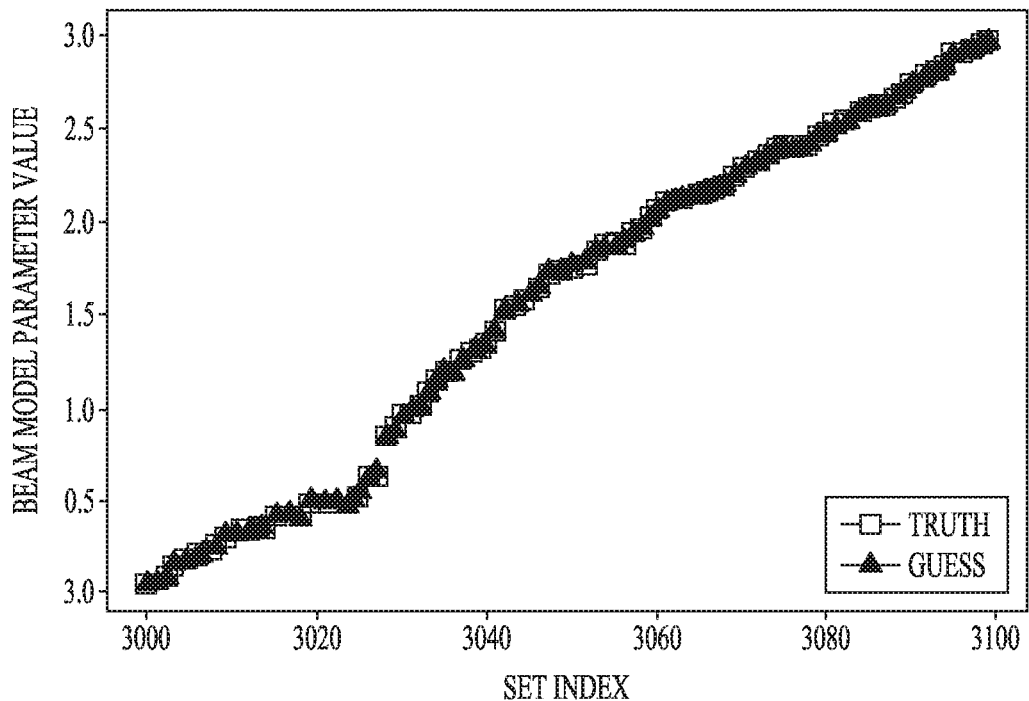
FIG. 6 illustrates an exemplary use a trained neural network model to estimate one beam model parameter.

FIG. 6 illustrates an example of results from using a trained neural network model to estimate one beam model parameter. In the example illustrated in FIG. 6, a number of sets of beam model parameter values can be provided, with a single beam model parameter that can vary between the sets. Additionally, one or more corresponding dose profiles having a field size of 5×5 can also be provided. In the example illustrated in FIG. 6, the estimated beam model parameter and the actual ground truth beam model parameter are plotted together. In the example illustrated in FIG. 6, approximately 3000 training sets were used to train the neural network model.

Figure 7A:
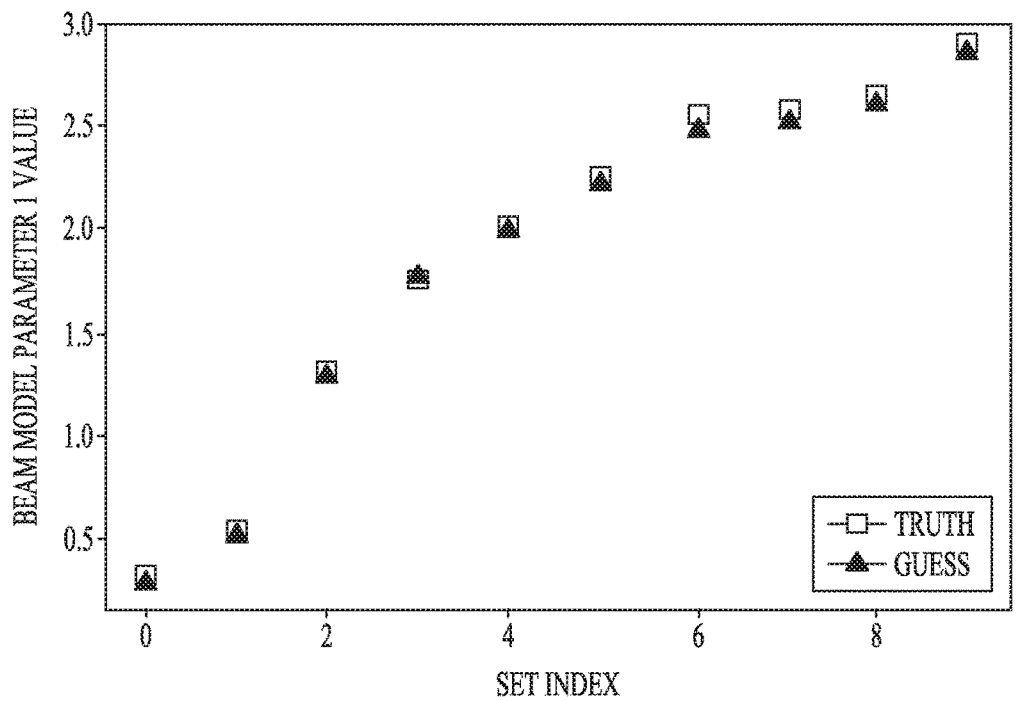
FIGS. 7A-7C illustrate an exemplary use of a trained neural network model to estimate three beam model parameters.
Figure 7B:
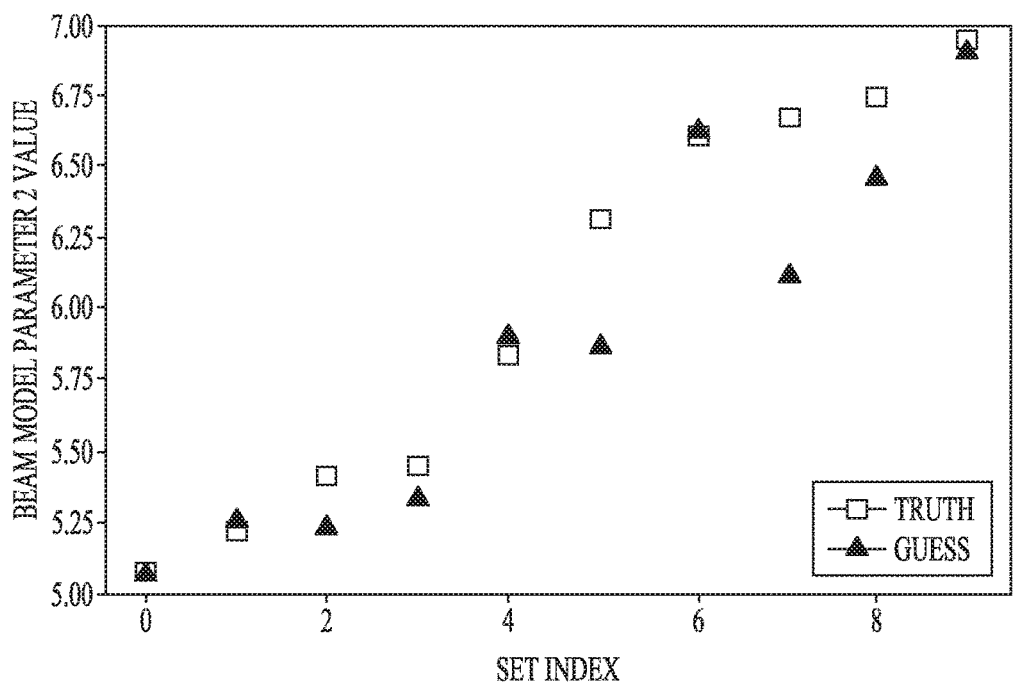
Figure 7C:
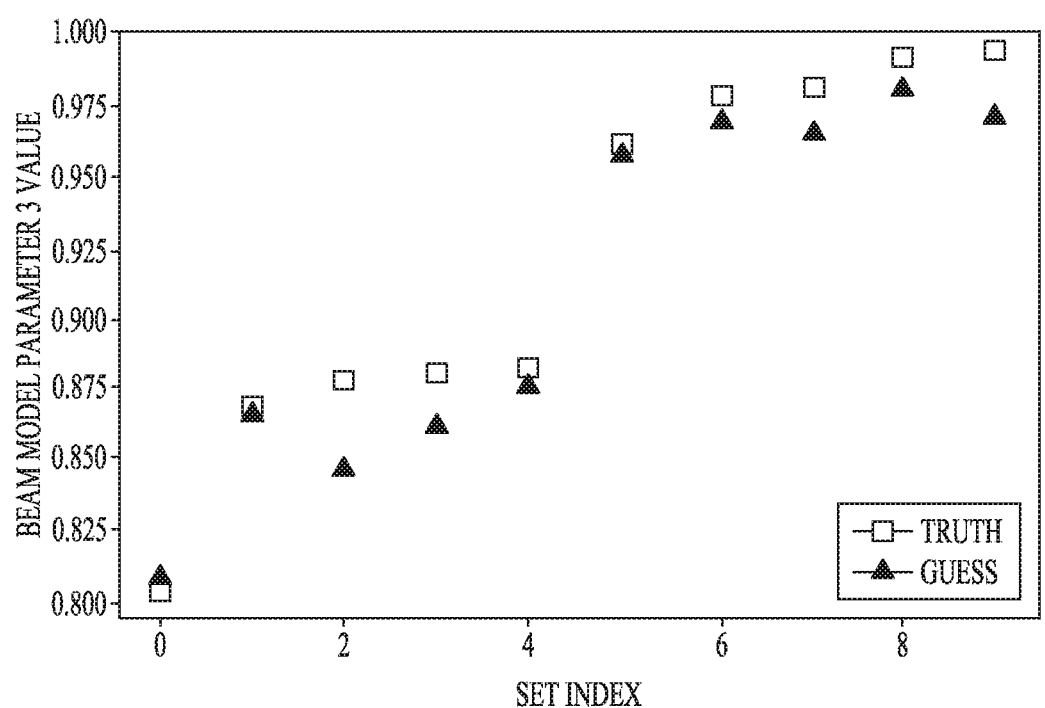

FIGS. 7A-7C illustrate an example of results from using a trained neural network to estimate three beam model parameter values. In the example illustrated in FIGS. 7A-7C, a number of sets of beam model parameter values can be provided. Six beam model parameter values can vary between the sets. Five dose profiles corresponding to five different field sizes can also be provided. In the examples illustrated in FIGS. 7A-7C, the estimated beam model parameter values and the actual ground truth beam model parameter values are plotted together. In the example illustrated in FIGS. 7A-7C6, approximately 10000 training sets were used to train the neural network model. Each of the training sets included 30 dose profiles, with each of the dose profiles corresponding to one of 5 different field sizes (e.g., 1×1, 2×2, etc.) and one of 6 different dose calculations (e.g., percent depth dose profile on-axis, percent depth dose profile off-axis, or radial dose profile).

Figure 8:
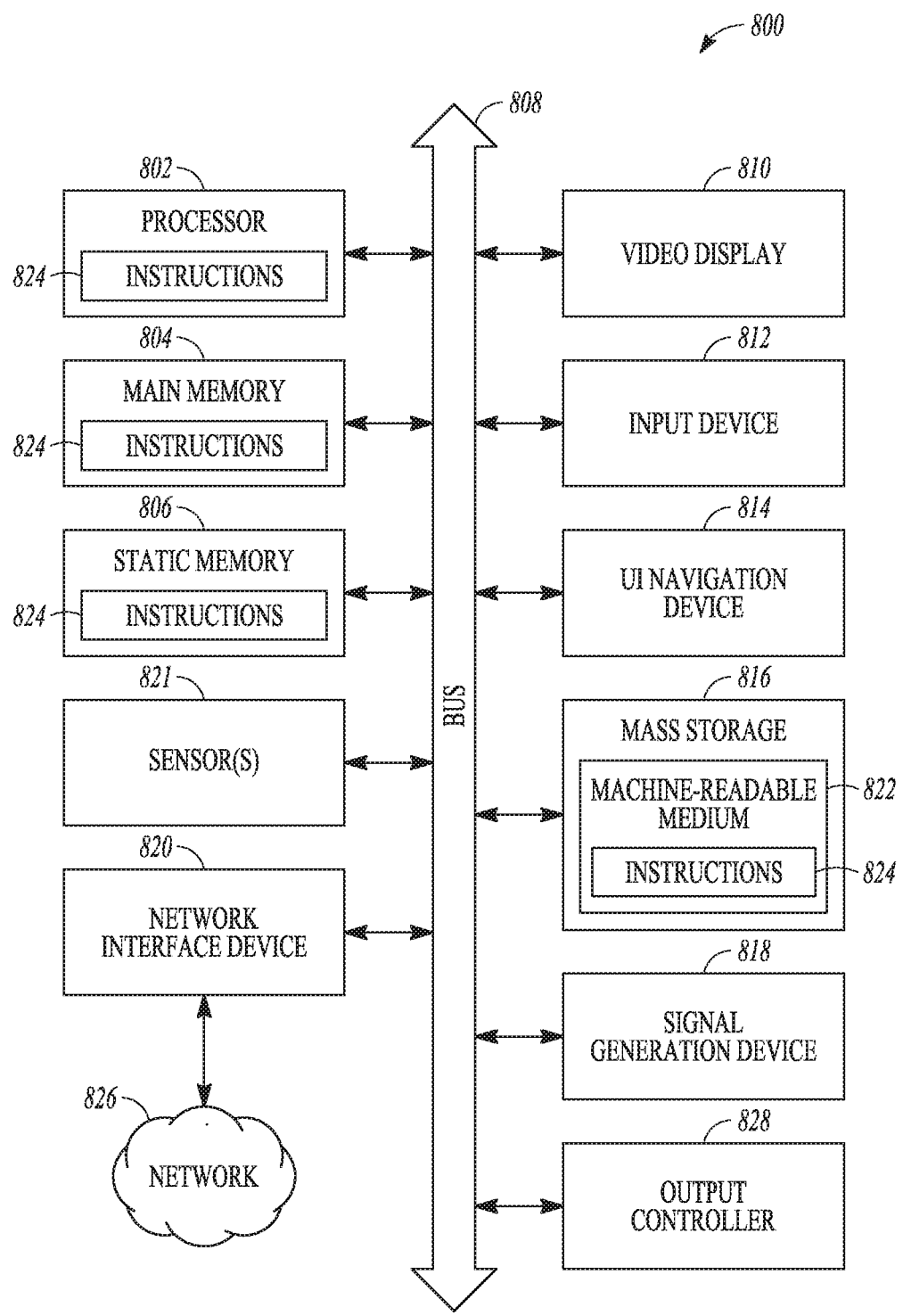
FIG. 8 illustrates an exemplary block diagram of a machine on which one or more of the methods as discussed herein can be implemented.

FIG. 8 illustrates a block diagram of an embodiment of a machine 800 on which one or more of the methods as discussed herein can be implemented. In one or more embodiments, one or more items of the image processing device 112 can be implemented by the machine 800. In alternative embodiments, the machine 800 operates as a standalone device or may be connected (e.g., networked) to other machines. In one or more embodiments, the image processing device 112 can include one or more of the items of the machine 800. In a networked deployment, the machine 800 may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example machine 80X) includes processing circuitry 802 (e.g., a central processing unit (CPU), a graphics processing unit (GPU), an application specific integrated circuit, circuitry, such as one or more transistors, resistors, capacitors, inductors, diodes, logic gates, multiplexers, buffers, modulators, demodulators, radios (e.g., transmit or receive radios or transceivers), sensors 821 (e.g., a transducer that converts one form of energy (e.g., light, heat, electrical, mechanical, or other energy) to another form of energy), or the like, or a combination thereof), a main memory 804 and a static memory 806, which communicate with each other via a bus 808. The machine 800 ((e.g., computer system) may further include a video display unit 810 (e.g., a liquid crystal display (LCD) or a cathode ray tube (CRT)). The machine 800 also includes an alphanumeric input device 812 (e.g., a keyboard), a user interface (UI) navigation device 814 (e.g., a mouse), a disk drive or mass storage unit 816, a signal generation device 818 (e.g., a speaker) and a network interface device 820.

The disk drive unit 816 includes a machine-readable medium 822 on which is stored one or more sets of instructions and data structures (e.g., software) 824 embodying or utilized by any one or more of the methodologies or functions described herein. The instructions 824 may also reside, completely or at least partially, within the main memory 804 and/or within the processor 802 during execution thereof by the machine 800, the main memory 804 and the processor 802 also constituting machine-readable media.

The machine 800 as illustrated includes an output controller 828. The output controller 828 manages data flow to/from the machine 800. The output controller 828 is sometimes called a device controller, with software that directly interacts with the output controller 828 being called a device driver.

While the machine-readable medium 822 is shown m an embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by was of example semiconductor memory devices. e.g., Erasable Programmable Read-Only Memory (EPROM), Electrically Erasable Programmable Read-Only Memory (EEPROM), and flash memory devices; magnetic disks such as internal hard disks and removable disks; magneto-optical disks, and CD-ROM and DVD-ROM disks.

The instructions 824 may further be transmitted or received over a communications network 826 using a transmission medium. The instructions 824 may be transmitted using the network interface device 820 and any one of a number of well-known transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

As used herein. "communicatively coupled between" means that the entities on either of the coupling must communicate through an item therebetween and that those entities cannot communicate with each other without communicating through the item.

Additional Notes

The above detailed description includes references to the accompanying drawings, which form a part of the detailed description. The drawings show, by way of illustration but not by way of limitation, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the invention or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," etc., are used merely as labels, and are not intended to impose numerical requirements on their objects.

Embodiments of the invention may be implemented with computer-executable instructions. The computer-executable instructions (e.g., software code) may be organized into one or more computer-executable components or modules. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

Method examples (e.g., operations and functions) described herein can be machine or computer-implemented at least in part (e.g., implemented as software code or instructions). Some examples can include a computer-readable medium or machine-readable medium encoded with instructions operable to configure an electronic device to perform methods as described in the above examples. An implementation of such methods can include software code, such as microcode, assembly language code, a higher-level language code, or the like (e.g., "source code"). Such software code can include computer readable instructions for performing various methods (e.g., "object" or "executable code"). The software code may form portions of computer program products. Software implementations of the embodiments described herein may be provided via an article of manufacture with the code or instructions stored thereon, or via a method of operating a communication interface to send data via a communication interface (e.g., wirelessly, over the internet, via satellite communications, and the like).

Further, the software code may be tangibly stored on one or more volatile or non-volatile computer-readable storage media during execution or at other times. These computer-readable storage media may include any mechanism that stores information in a form accessible by a machine (e.g., computing device, electronic system, and the like), such as, but are not limited to, floppy disks, hard disks, removable magnetic disks, any form of magnetic disk storage media, CDROMS, magnetic-optical disks, removable optical disks (e.g., compact disks and digital video disks), flash memory devices, magnetic cassettes, memory cards or sticks (e.g., secure digital cards), random access memories (RAMs) (e.g., CMOS RAM and the like), recordable/non-recordable media (e.g., read only memories (ROMs)), EPROMS, EEPROMS, or any type of media suitable for storing electronic instructions, and the like. Such computer readable storage medium coupled to a computer system bus to be accessible by the processor and other parts of the OIS.

In an embodiment the computer-readable storage medium may have encoded a data structure for a treatment planning, wherein the treatment plan may be adaptive. The data structure for the computer-readable storage medium may be at least one of a Digital Imaging and Communications in Medicine (DICOM) format, an extended DICOM format, a XML format, and the like. DICOM is an international communications standard that defines the format used to transfer medical image-related data between various types of medical equipment. DICOM RT refers to the communication standards that are specific to radiation therapy.

In various embodiments of the invention, the method of creating a component or module can be implemented in software, hardware, or a combination thereof. The methods provided by various embodiments of the present invention, for example, can be implemented in software by using standard programming languages such as, for example, C, C++, Java, Python, and the like; and combinations thereof. As used herein, the terms "software" and "firmware" are interchangeable, and include any computer program stored in memory for execution by a computer.

A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present invention also relates to a system for performing the operations herein. This system may be specially constructed for the required purposes, or it may comprise a general purpose computer selectively activated or reconfigured by a computer program stored in the computer. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In view of the above, it will be seen that the several objects of the invention are achieved and other advantageous results attained. Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

What is claimed is:

1. A computer implemented method for training a deep convolutional neural network model to provide a beam model for a radiation machine to deliver a radiation treatment dose to a subject, the method comprising:
   determining a range of parameter values for at least one parameter of a beam model corresponding to the radiation machine;
   generating a plurality of sets of beam model parameter values, wherein one or more individual sets of beam model parameter values includes a parameter value selected from the determined range of parameter values;
   providing a plurality of corresponding dose profiles respectively corresponding to respective individual sets beam model parameter values in the plurality of sets of beam model parameter values; and
   training the neural network model using the plurality of beam models and the corresponding dose profiles.

2. The method of claim 1 comprising training the neural network model using at least one set of beam model parameter values and corresponding measured dose profiles previously collected from at least one radiation machine.

3. The method of claim 1 wherein determining the range of beam model parameter values for at least one beam model parameter includes determining a beam model parameter value for each of a plurality of radiation machines.

4. The method of claim 1 comprising measuring at least one dose profile for each of a plurality of radiation machines.

5. The method of claim 4 wherein training the neural network model includes:
   providing N sets of generated beam model parameter values and corresponding dose profiles to the neural network model; and
   providing dose profiles from M radiation machines and corresponding beam model parameters to the neural network model.

6. The method of claim 1 comprising randomly or pseudo-randomly selecting the beam model parameter value, from the determined range of beam model parameter values, for generating at least one of the sets of beam model parameter values.

7. The method of claim 1 wherein respective sets of beam model parameter values are generated using a plurality of dose profiles, wherein an individual dose profile of the plurality of corresponding dose profiles includes a relative dose of radiation that varies with depth into a target sample.

8. The method of claim 1 wherein determining a range of beam model parameter values for at least one parameter of a beam model includes determining a plurality of beam model parameter values related to an energy distribution of photons emitted from a radiation source of the radiation machine.

9. The method of claim 8 wherein the beam model parameters include at least one of a size of a radiation source, a position of a radiation source, or an energy spectrum of a radiation source.

10. The method of claim 1 wherein determining a range of beam model parameter values for at least one parameter of a beam model includes determining a plurality of beam model parameter values related to an energy distribution of electrons emitted from a radiation source of the radiation machine.

11. A computer implemented method of using a deep convolutional neural network to determine at least one parameter value of a beam model for a radiation machine, the method comprising:
   receiving a trained neural network model previously trained using a plurality of sets of beam model parameter values and corresponding dose profiles, the trained neural network model being trained for predicting at least one radiation machine beam model parameter value from one or more measured radiation machine dose profiles;
   measuring a plurality of dose profiles from the radiation machine to be provided as an input to the trained neural network model; and
   determining at least one beam model parameter value of a set of beam model parameter values for the radiation machine using the trained neural network model.

12. The method of claim 11 comprising calculating a dose profile from a set of beam model parameter values that includes the determined at least one beam model parameter value and comparing the calculated dose profile to a measured dose profile.

13. The method of claim 12 wherein the set of beam model parameter values includes at least one beam model parameter value that is not determined using the trained neural network model.

14. The method of claim 12 comprising updating the at least one beam model parameter value determined by the neural network model if a difference between the measured dose profile from the radiation machine and the determined dose profile meets a specified criterion.

15. The method of claim 12 comprising:
   determining a plurality of dose profiles using a set of beam model parameter values that includes the at least one beam model parameter value determined by the neural network model, individual ones of the plurality of dose profiles corresponding to a different field size of the radiation machine; and
   comparing each of the plurality of determined dose profiles to a corresponding one of a plurality of measured dose profiles.

16. The method of claim 11, wherein receiving a neural network previously trained using a plurality of sets of beam model parameter values and corresponding dose profiles includes receiving a trained neural network previously trained according to a method that includes:
   determining a range of beam model parameter values for at least one parameter of a beam model corresponding to the radiation machine;
   generating a plurality of sets of beam model parameter values, wherein one or more individual sets of beam model parameter values includes a parameter value selected from the determined range of parameter values;
   providing a plurality of corresponding dose profiles respectively corresponding to respective individual sets of beam model parameter values in the plurality of sets of beam model parameter values; and
   training the neural network using the plurality of sets of beam model parameter values and the corresponding dose profiles.

17. The method of claim 11 comprising using the set of beam model parameter values with the determined at least one beam model parameter value to estimate a dose of radiation from the radiation machine to target region within a patient.

18. A system for generating at least beam model parameter value of a beam model for a radiation machine from at least one measured dose profile of the radiation machine, the system comprising:
   an interface configured to receive at least one measured dose profile corresponding to the radiation machine and receive a neural network model for estimating at least one beam model parameter value of the radiation machine;
   a memory for storing the neural network model and the at least one measured dose profile, wherein the neural network model is trained using a plurality of sets of beam model parameter values and corresponding dose profiles; and
   a processor configured to estimate at least one beam model parameter value of the radiation machine using the at least one measured dose profile as an input to the neural network model.

19. The system of claim 18, wherein the stored neural network model is trained by determining a range of beam model parameter values for at least one parameter of a beam model corresponding to the radiation machine, generating a plurality of sets of beam model parameter values, wherein one or more individual sets of beam model parameter values includes a parameter value selected from the determined range of parameter values, providing a plurality of corresponding dose profiles respectively corresponding to respective individual sets of beam model parameter values in the plurality of sets of beam model parameter values; and providing the plurality of sets of beam model parameter values and the corresponding dose profiles to the neural network model.

20. The system of claim 18 wherein the interface is configured to transmit a set of beam model parameter values including the beam model parameter value estimated by the neural network model and corresponding dose profiles to a user if a difference between the measured dose profile from the radiation machine and a dose profile determined from the set of beam model parameter values meets a specified criterion.

\* \* \* \* \*